Figures 1, 2, 3, 4, 5, 6, 7, 8, 9, 10, 11, 12, 13, 14:
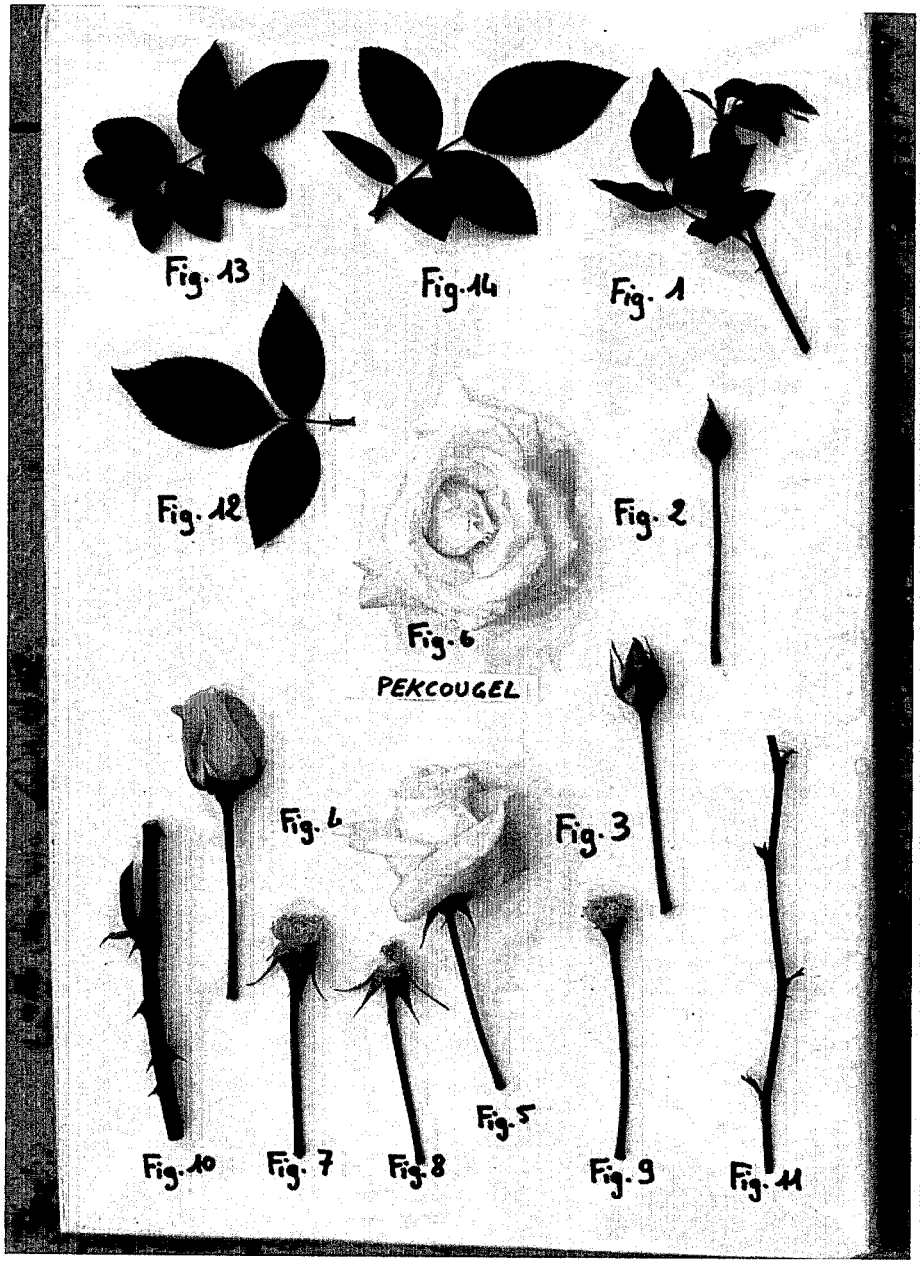

US00PP08277P

United States Patent [19]

Pekmez

[11] Patent Number: Plant 8,277

[45] Date of Patent: Jun. 29, 1993

[54] HYBRID TEA ROSE PLANT NAMED PEKCOUGEL

[76] Inventor: Paul Pekmez, La Petite Pierre, 67290 Wingen-sur-Moder, France

[21] Appl. No.: 813,150

[22] Filed: Dec. 23, 1991

[51] Int. Cl.[5] ..... A01H 5/00

[52] U.S. Cl. ..... Plt./11

[58] Field of Search ..... Plt. 11, 12, 14, 18, Plt./22, 23, 26

*Primary Examiner*—Howard J. Locker

*Attorney, Agent, or Firm*—Christie, Parker & Hale

[57] ABSTRACT

A new hybrid tea rose with near white flowers.

SUMMARY OF THE INVENTION

The present invention relates to a new and distinct variety of rose plant of the hybrid tea rose class which was originated by my crossing as seed parent the variety known as 'Coquette' (U.S. Plant Pat. No. 4,019) and as pollen parent an unnamed and unpatented seedling of my creation. The varietal denomination of this new rose is 'Pekcougel'.

Among the novel characteristics possessed by this new variety which distinguishes it from its parents and all other varieties of which I am aware are its attractive well formed near white flowers borne on a plant suitable for cut flower production and for growing outdoors in gardens. Flowers are 4 to 5 cm. in size and open well and hold their coloring as blooms age. Asexual reproduction by propagation by budding of the new variety as performed in La Petite Pierre, Wingen-Sur-Moder, France, shows that the foregoing and other distinguishing characteristics come true to form and are established and transmitted through succeeding propagations.

1 Drawing Sheet

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character. As can be seen there is described a young stem shoot 1, green bud 2, buds showing color 3 and 4, opening flower 5, open flower 6, reproductive organs 7, 8 and 9, stems with prickles and thorns 10 and 11, and compound 3, 7 and 5 leaflet leaves 12, 13 and 14.

DESCRIPTION OF THE NEW VARIETY

Pekcougel is an unusually fine hybrid tea rose of near white to light pink flower coloration. It is well suited both for growing in gardens and for cut flower production under glass. The buds are well shaped and of good form. The foliage is dark green, brilliant and dense.

The following is a detailed description of my new variety, with color terminology in accordance with The Royal Horticultural Society Colour Chart (R.H.S.C.C.). The terminology used in color description herein refers to plate numbers in the aforementioned color chart.

Parentage: Seedling.

*Seed parent.*—'Coquette'.

*Pollen parent.*—Unnamed seedling.

Class: Hybrid tea.

The following information is from observations made of specimens grown outdoors in La Petite Pierre, France.

FLOWER

Blooming habit: Recurrent.

A. Bud:

(1) *Size.*—Medium.

(2) *Form.*—Long pointed.

(3) *Color.*—As sepals divide, bud color is near 53A, until petals begin to unfurl.

(4) *Sepals.*—Slightly longer than bud, generally simple.

(5) *Peduncle.*—Length: In proportion to bloom. Aspect: Straight. Strength: Erect. Color: Dark green with bronze hue.

B. Bloom:

(1) *Size.*—Average size when fully expanded — about 4 to 5 cm.

(2) *Borne.*—Singly, one to a stem, disbudded.

(3) *Form.*—High centered at first, becoming flat. Outer petals quill to points, others roll under.

(4) *Petalage.*—Number of petals under normal conditions — about 30 to 35.

(5) *Color.*—After sepals fall and petals begin to unfurl, bud color lightens to near 49B. As flower opens, predominant flower color viewing petals' top surface is near white 155D with light pink at apices of outer petals and offwhite/light beige where petals bunch. Color of petal undersurface shows light pink, near 56C to D which extends to outer petal to surfaces. Overall coloration has a light pink affect.

C. Petals:

(1) *Texture.*—Medium to thick.

(2) *Appearance.*—Inside velvety and outside satiny.

(3) *Form.*—Broad, fan shaped with some indentation or undulation at margin.

(4) *Arrangement.*—Regularly arranged, imbricated.

(5) *Petaloids in center.*—Few.

(6) *Persistence.*—Petals persist and flowers open slowly which is desirable in cut flowers.

(7) *Fragrance.*—Slight.

(8) *Lasting quality.*—Very long lasting on plant and as cut flower.

REPRODUCTIVE ORGANS

A. Stamens, filaments and anthers:
*Arrangement.*—Regularly arranged around styles.
*Color.*—Orange yellow.

B. Pollen:
*Color.*—Yellow.

C. Styles: Medium length.

D. Stigmas:
*Color.*—Orange red.

E. Hips: None observed.

PLANT

A. Form: Well shaped, symmetrical.

B. Growth: Vigorous.
*Height attained.*—About 80 to 100 cm.

C. Foliage: Compound 3, 5 and 7 leaflets.
(1) *Size.*—Medium.
(2) *Quantity.*—Abundant.
(3) *Color.*—New foliage: Upper side — near 139A. Under side — near 139B. Old foliage: Upper side — near 139A. Under side — near 139B.
(4) *Shape.*—Oval, pointed.
(5) *Texture.*—Leathery; upper side is glossy; under side is matte.

(6) *Edge.*—Lightly serrate.
(7) *Serration.*—Ordinary.
(8) *Leaf stem.*—Color — dark green.
(9) *Stipules.*—Medium length, simple.
(10) *Resistance to disease.*—Mildew — good.

D. Wood:
(1) *New wood.*—Color — dark green with bronze tint. Bark — smooth.
(2) *Old wood.*—Color — dark green. Bark — smooth.

E. Thorns:
*Quantity (main stalk).*—Ordinary.
*On laterals from stalk.*—Few.
*Form.*—Long, recurved.
*Length.*—Medium.
*Color.*—Near tan.
*Position.*—Irregular.
*Prickles.*—Few to none present.

F. Winter hardiness: Needs protection in severe climates.

I claim:

1. A new and distinct variety of rose plant of the hybrid tea rose class, substantially as shown and described.

* * * * *

PEKCOUGEL